United States Patent

Anderson

[11] Patent Number: 4,571,085
[45] Date of Patent: Feb. 18, 1986

[54] REFLECTOMETER BASED ON OPTICAL CAVITY DECAY TIME

[75] Inventor: Dana Z. Anderson, Pasadena, Calif.

[73] Assignee: California Institute of Technology, Pasadena, Calif.

[21] Appl. No.: 540,788

[22] Filed: Oct. 11, 1983

[51] Int. Cl.[4] ............................................. G01N 21/55
[52] U.S. Cl. ..................................... 356/445; 356/124
[58] Field of Search ............... 356/445, 345, 346, 352, 356/350, 124; 372/25, 109, 12

[56] References Cited

U.S. PATENT DOCUMENTS

| | | | |
|---|---|---|---|
| 3,737,231 | 6/1973 | Low et al. | 372/25 |
| 3,927,946 | 12/1975 | McClure | 356/350 |
| 4,019,156 | 4/1977 | Fountain et al. | 372/12 X |
| 4,136,954 | 1/1979 | Jamieson | 356/346 X |
| 4,176,327 | 11/1979 | Wayne et al. | 372/12 |

OTHER PUBLICATIONS

Virgil Sanders, High-Precision Reflectivity Measurement Technique for Low-Loss Laser Mirrors, Applied Optics, vol. 16, No. 1, Jan. 1977, pp. 19 and 20.
J. M. Herbelin, et al., Sensitive Measurement of Photon Lifetime and True Reflectances in an Optical Cavity by a Phase-Shift Method, Applied Optics, vol. 19, No. 1, Jan. 1, 1980, pp. 144–147.
J. M. Herbelin, et al., Development of Laser Mirrors of Very High Reflectivity Using the Cavity-Attenuated Phase-Shift Method, Applied Optics, vol. 20, No. 19, Oct. 1, 1981, pp. 3341–3344.

*Primary Examiner*—Vincent P. McGraw
*Assistant Examiner*—Robert D. V. Thompson, III
*Attorney, Agent, or Firm*—Freilich, Hornbaker, Rosen & Fernandez

[57] ABSTRACT

A method and apparatus for making decay time measurements of an optical cavity having at least two reflecting optical elements by directing a beam of light into the cavity, switching the beam of light off when the intensity in the cavity reaches a predetermined threshold level, monitoring the beam intensity decay of the optical cavity, and measuring the intensity decay time either with a storage oscilloscope or a digital counter.

11 Claims, 4 Drawing Figures

REFLECTOMETER BASED ON OPTICAL CAVITY DECAY TIME

ORIGIN OF INVENTION

The invention described herein was supported by a National Science Foundation Grand PHY-8204056.

BACKGROUND OF THE INVENTION

This invention relates to a method and apparatus for making reflectivity measurements of low-loss highly reflecting coatings, and transmission measurements of low-loss antireflection coatings on optical elements based upon the intensity decay time of an optical cavity which includes the elements. The method has utility in testing optical cavities such as those employed in ring laser gyroscopes.

Low-loss optical coatings often play a crucial role in the performance of optical instruments. Unfortunately, coating characteristics can vary considerably batch to batch from a single manufacturer and drastically manufacturer to manufacturer, even when the coatings are required to meet identical specifications. For this reason, it may be useful for a manufacturer or to a customer to have on hand apparatus which can measure coating characteristics rather than rely upon the specfications for the coating.

An object of this invention is to provide a method and apparatus for measuring the reflectivity of highly reflecting coatings (having reflectivity approaching 1), or to measure the transmission of low-loss antireflection coatings (on low-loss substrates). Seemingly straightforward techniques, such as measuring the small change in incident light intensity with a power meter, have proven unreliable. A technique for measuring reflectance suggested by Virgil Sanders, Appl. Opt. 16 19, (1977) works well for moderate loss optical elements, but less so when losses are very low. That technique measures total reflection loss of polarized light using two intralaser cavity measurements, one with the sample mirror and one without, by varying the angle $\theta$ of a rotatable window in the path of the beam in the cavity from Brewster's angle until the laser action is quenched in both directions. The difference in the included angle for the two measurements is a measure of the total loss in the sample mirror.

The method of the present invention, based on optical cavity decay time, is reliable, and in fact becomes more accurate with decreasing losses. Because of its accuracy, it is also useful in testing optical cavities, e.g., those used to implement what has come to be known as ring laser gyroscopes. The fundamental quantity measured is the cavity decay time. From this quantity, other characteristics, such as mirror reflectivity, can be inferred.

A different technique developed by J. M. Herbelin, et al., Appl. Opt. 19 144 (1980) and Appl. Opt. 20 3341 (1981), obtains the cavity decay time through a measurement of the phase retardation of an intensity modulated CW laser induced by an optical cavity. That technique transmits the intensity modulatd CW laser beam through the cavity, and measures any shift in the phase of the transmitted modulation as a measurement of effective photon lifetime in the optical cavity.

SUMMARY OF THE INVENTION

In accordance with the present invention, the intensity decay time of an optical cavity of two or more reflecting elements, or at least partially reflecting elements, is measured by directing a beam of light from a source into the optical cavity through a beam switch, turning the beam switch to the "off" condition when the beam intensity out of the cavity reaches a predetermined threshold level, and monitoring the intensity of light in the optical cavity for measurement of the intensity decay time, either with a storage oscilloscope, the sweep of which is triggered by the signal that switches the beam switch off, or with any timing mechanism that is turned on after decay of the monitored intensity to a first predetermined level $V_c$, and off after further decay to a second predetermined level that is a predetermined fraction of the first level, preferably equal to $(1/e) V_c$. Any one of various cavity parameters may be determined from formulae relating them to the cavity decay time. By making a number of measurements with an appropriate number of mirrors, one can always obtain the characteristics of each individual mirror.

The novel features of the invention are set forth with particularity in the appended claims. The invention will best be understood from the following description when read in connection with the accompanying drawings.

DESCRIPTION OF PREFERRED EMBODIMENTS

Figure 1:
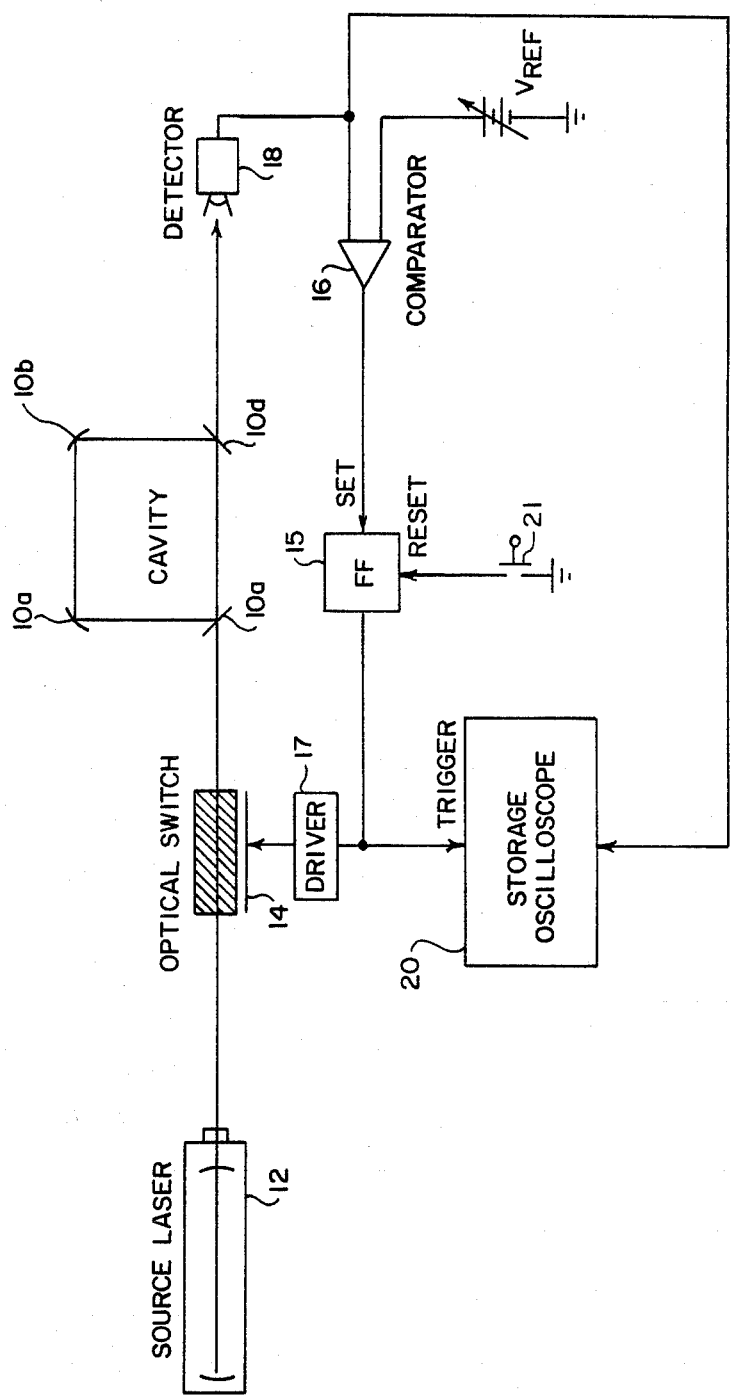
FIG. 1 illustrates a schematic diagram of decay measuring apparatus in accordance with the present invention.

FIG. 1 illustrates schematically the method and apparatus of the invention. The technique relies on the fact that with no light incident upon a cavity 10, after a beam of light has been injected, its output is determined only by the cavity's transient response, which is characterized by an exponential decay of the intensity with a time constant, which in turn is determined only by the round trip losses in the cavity, the round trip path length of the cavity and the speed of light. Therefore, if light is injected into the cavity from a source laser 12 through an optical switch 14, such as an acousto optic cell, and then the source is quickly shut off by setting a bistable circuit (flip-flop) 15 once the injected light reaches a predetermined reference level, as determined by a comparator 16 connected to a light detector 18, the decay time can be measured with suitable measuring means, such as storage oscilloscope 20 (Tektronix Model 468) the sweep of which is triggered on when the beam switch 14 is turned to its "off" state by the comparator 16 via a driver 17 at the instant the output of the detector 18 exceeds a reference voltage, $V_{REF}$. The switch 14 is not turned on again to transmit the laser beam until the flip-flop is reset by a switch 20'. The storage oscilloscope automatically resets when the flip-flop 15 is again set to trigger the oscilloscope for another cycle. Measuring the round-trip path length is easy; with these two numbers in hand the cavity losses can be deduced.

The fundamental quantity measured by this technique is cavity decay time. From this quantity, other characteristics, such as mirror reflectivity, can be inferred. To obtain the mirror losses due to scattering and absorption of one of the mirrors 10a and 10b in the cavity, one must make a separate measurement of their transmission, which can be done with reasonable precision using a power meter having a large dynamic range (or having calibrated attenuators) by measuring the incident intensity with and without the mirror in the light path. On the other hand, in many applications it may be the actual cavity characteristics which are of interest, rather than the mirrors which comprise it, in which case the latter step is unnecessary. Losses of antireflection coatings can be determined by placement in the optical path of a previously characterized cavity.

To understand the theory of the present invention, imagine an optical cavity which has been injected with light. In a classical sense, one may think of the injected light as traveling round and round or back and forth in a cavity. With each round trip, a fraction of the light is lost due to the reflecting (or antireflecting) characteristics of cavity elements. From this it is apparent that the light at a given point will decay in steps spaced a round-trip time apart with a fractional height dictated by the round-trip losses. With a somewhat greater intuition it is also apparent that if the losses are small, i.e., if the step size is small, then the decay will be exponential. From the more detailed consideration, it is seen that this is indeed the case, and that decay time depends only on the round-trip time and the fractional losses. Small fractional changes in cavity length caused, for example, by acoustical vibrations can only make small fractional changes in the decay time. The frequency of the light will affect decay time only insofar as the fractional losses, or round-trip time, depend upon frequency.

As just noted above, the transient response of the cavity is exponential only in the case of low total cavity losses. For example, a 10% total cavity loss implies a standard error of about 1% for an exponential fit to the cavity decay. Practical considerations (namely electronic speed) put a more stringent constraint on the maximum measureable loss; so this technique is appropriate only when cavity losses are small. In the following discussion, a low-loss condition is assumed throughout.

There are several ways in which a mirror coating can be characterized, the choice of which often depends upon whether the mirror itself or its intended use is to be emphasized. As for the mirror itself, it will suffice for the present invention to ascribe to it three parameters, R, S and T, the intensity reflection, loss and transmission coefficients, respectively. The term "loss" and symbol S are used to represent the nonrecoverable energy losses from scattering and absorption, and do not include transmission so that the coefficients are related through energy conservation by $R+S+T=1$. The term "total loss" is used to mean the sum, $S+T=L$, for a given mirror or for the cavity losses, including transmission, as a whole. A mirror may also exhibit amplitude and phase birefringence with respect to the direction of polarization. In general the mirror coefficients will depend on the direction of incidence and wavelength as well; all these dependences can be controlled during test measurements to within tolerances of the measuring equipment and therefore will be dropped for the following discussion.

Once the decay time, $\tau_c$, has been measured, one can infer the mirror reflectivity, or any number of parameters which describe the cavity losses from the formulae in the table below which gives various cavity parameters in terms of the decay time in the low total low loss limit are summarized in the following table.

| PARAMETER | SYMBOL | FORMULA |
| --- | --- | --- |
| Cavity Linewidth (full width at half maximum intensity) | $\Delta \nu$ | $(2\pi\tau_c)^{-1}$ |
| Cavity Quality Factor | Q | $2\pi\nu\tau_c$ |
| Finesse (ratio of the cavity free spectral range to the intensity response function $\Delta\nu$) | F | $2\pi k$ |
| Total Cavity Loss (including transmission) | L | $k^{-1}$ |
| Mirror Reflectivity Product | R | $\left(1 - \frac{1}{2k}\right)^2$ |
| Mirror Reflectivity (Two-mirror cavity with identical mirrors) | R | $1 - \frac{1}{2k}$ |

In the table relating the cavity intensity decay time, $\tau_c$, to such parameters as Finesse, F, (defined as the ratio of the cavity free spectral range to the intensity response function full width at half maximum, $\Delta\nu$) the round-trip number k is defined as $(c/L)\tau_c$, and L is the round-trip optical path. It should be kept in mind that these formulae have been derived in the limit of low total loss.

Figure 2:
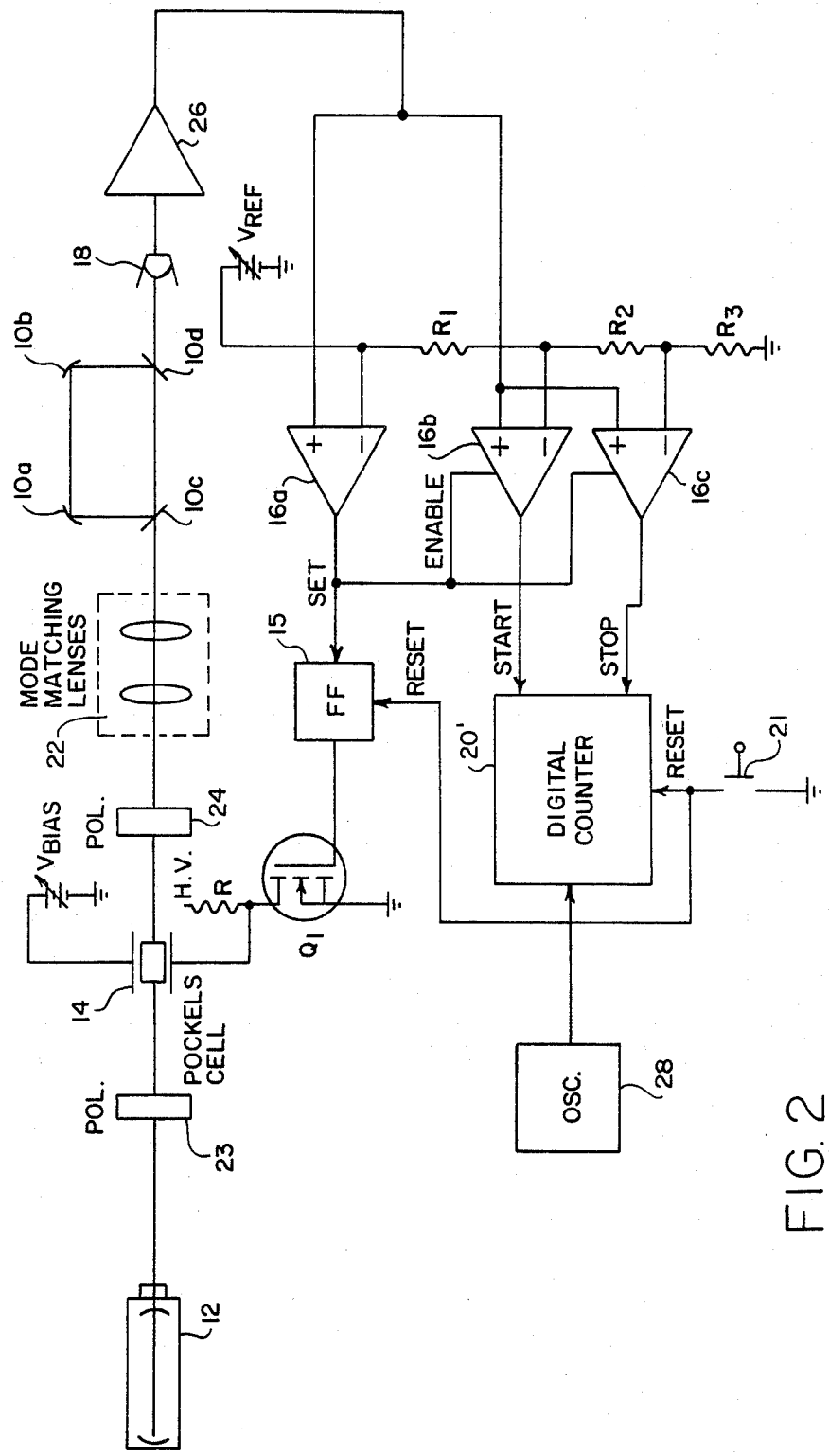
FIG. 2 is a schematic of a preferred implementation of apparatus for cavity decay time measurement.

It has been shown that mirror reflectivities can be obtained by measuring the transient response of the cavity and the cavity length, and it is clear that under certain conditions the transient response of the cavity will dominate the output of the cavity. The general design of two exemplary embodiments are shown in FIGS. 1 and 2. In the description that follows, the requirements on the individual components necessary to meet the above conditions, and to have optimum performance, are discussed.

The apparatus illustrated in FIG. 1 is shown with a modification in FIG. 2 using the same reference numerals for the same components. In brief summary of the operation of the instrument: light from the source laser 12 impinges upon a cavity mirror. If the laser light can be made to be at a resonant frequency of the cavity for a resonable amount of time, such as when sweeping a CW laser or a pulsed laser with a substantially long pulse period, then light will build inside the cavity and be transmitted through the mirrors of the cavity. The detector 18 senses the intensity of the light transmitted through one of the mirrors. When the transmitted light reaches a predetermined level, the laser light is switched off via the switch 14 which is an acousto optic cell in the embodiment of FIG. 1. At the same time, the storage oscilloscope 20 is triggered on, as noted hereinbefore, and the decay time from some level $V_c$ to a level at some predetermined fraction of $V_c$ is determined directly on the oscilloscope.

The wavelength of the source laser must, of course, be that for which the mirrors are designed. However, the stability requirements are not severe. Frequency drift is even desirable. In practice, the laser may be allowed to drift into cavity resonance, thus precluding the need for some means of frequency control or sweeping mechanism.

The mode matching system comprised of mode matching lenses 22 are designed so that the laser and cavity fundamental modes are well coupled. In most cases it has been found that the mode matching is not extremely critical, but it serves three purposes. (1) In the case of a weak source laser (such as most He—Ne lasers) it is necessary to maximize the output intensity of the cavity and thereby minimize the subsequent requirements on amplifier of gain and signal to noise ratio. (2) It may also be necessary to discriminate against off-axis (m and/or n$\neq$0) cavity modes. In principle, as long as no apertures are present and the mirror surfaces are large, the decay time for all modes is the same. On the other hand, off-axis modes have an effectively larger cross-sectional area and therefore sample a larger surface area on the mirror than do longitudinal ($m,n=0$) modes. Thus in practice these mode types may have different decay times. (3) Proper mode matching also minimizes the chance of multiple cavity spatial mode excitation. However, if the photodetector area is large compared to the spot size, it will detect no interference between modes having the same mode number even though they may have different frequencies; i.e., the detector sees only the decay of the sum of the intensities of the various modes. Still, if their decay times are different, the net intensity decay can appear nonexponential. In any case, it is probably best if the longitudinal mode coupling is the largest.

In the embodiment of FIG. 2, the optical switch 14 consists of a Pockels cell (Coherent Inc. Mod 28) sandwiched by a pair of crossed polarizers 23, 24. The Pockels cell drive is a high-speed high-voltage MOSFET switch $Q_1$. This switch must, of course, be capable of switching a high voltage ($\sim$200 Volts) necessary for the Pockels cell in a time rather short compared to the cavity decay time. The voltage bias on the cell is adjusted so that when the high voltage MOSFET switch $Q_1$ is off, no light is transmitted through the second polarizer. With the MOSFET switch on, maximum light is transmitted. The second polarizer determines the state of polarization which will enter the cavity.

The cavity itself can, in general, have any desired geometry, with either a round-and-round arrangement of three or more elements or a back-and-forth arrangement with two or more elements. In each geometry, it is best to use the highest two transmitting mirrors as input and output elements if the mirrors of the set are not nominally identical. Motions of the mirrors due, for example, to mechanical vibrations are usually small over time scales of the cavity decay time. Once the light is switched off, motion of the mirrors cannot significantly change the decay time since the fractional change in cavity length due to vibration is negligible.

In this second embodiment, a digital clock 20' is used in place of the storage oscilloscope to measure the decay time from $V_c$ set by the ratio of the sum of two voltage dividing resistors ($R_2+R_3$) to the sum of all three voltage dividing resistors ($R_1+R_2+R_3$) to (1/e) $V_c$, where $1/e =R_3/(R_2+R_3)$, as shown in FIG. 2, although the fraction does not need to be 1/e; it can be anything less than one, as long as an appropriate conversion factor is introduced in the formulae of the table above, to relate measured time to the characteristic decay 1/e time, $\tau_c$. The electronic circuit which drives the counter, and the counter itself, is the most critical part of the apparatus, simply because it must be fast. Typical decay times of low loss cavities may be from 0.1 to 50 $\mu$s. The precision of the measurement is directly determined by the speed of the electronic circuit and counter.

Figure 3:
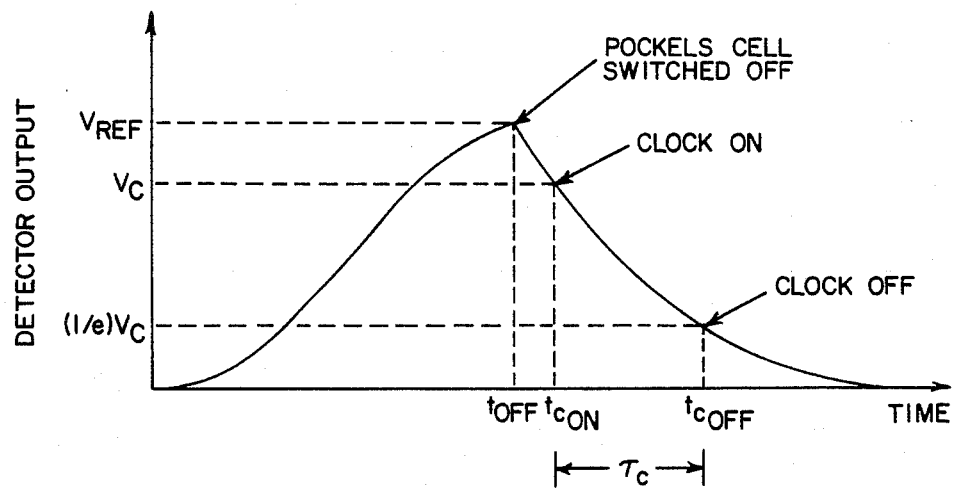
FIG. 3 illustrates comparator timing in which comparator 1 turns the Pockels device of FIG. 2 off when detector output reaches $V_{off}$ and comparator 2 turns the clock on at $V_{on}$, and comparator 3 turns the clock off when the detector output falls to $1/e\ V_{clock}$.

The front end of the electronic circuit consists of a silicon photodetector 18 (Centronics BPX 65) followed by a low noise wideband preamplifier 26 (Comlinear CL103AI). The output of the amplifier is fed to a set of three comparators 16a, 16b, 16c in parallel, but only the first comparator 16a is enabled. The other two comparators 16b and 16c are disabled until the detector output from the amplifier 26 exceeds a reference voltage $V_{REF}$. The output of the comparator 16a then switches the MOSFET switch $Q_1$ off, thus switching the Pockels cell off. That output also enables the comparators 16b and 16c to start and stop the clock counter as the decaying output falls below the level $V_c$ and 1/e $V_c$, respectively. FIG. 3 shows the event timing of the comparators.

Because there is a short delay before the light shuts off once the MOSFET switch is turned off, the clock does not begin timing until the detector level falls below the second threshold $V_c$ set at the comparator 16b somewhat lower than the first reference $V_{REF}$. The threshold on the third comparator 16c is set at (1/e) $V_c$. When this third comparator fires, and the clock ceases timing, the decay time is displayed directly. After this time is recorded, the timing cycle may be restarted by resetting the clock. In order that the Pockels cell not be turned on again as the detector output decays below the level $V_{REF}$ which switched the MOSFET switch off, the bistable circuit (flip-flop) 15 is interposed between the comparator 16a so that the MOSFET switch is turned off when the comparator switches the bistable circuit to the set state. Thereafter, the MOSFET switch may be turned on again for another cycle by resetting the bistable circuit with the reset switch 21 which also resets the counter.

It is best to adjust the threshold of the first comparator 16a so that only events with the highest intensity trigger the cycle. One can do this by first setting the threshold high, then slowly reducing it until the circuit triggers. One should then have a good working threshold level. Multimode events caused by fast laser drift or large and fast cavity mirror motions tend to be less intense since the laser light is spending relatively less time on resonance than when drift and motions are slow and small. By setting the threshold high one avoids most undesirable (nonexponential) events.

In this circuit the comparators are specified as having a 14 to 20 nsec propagation delay. If overall timing accuracy needs to be much better than 10 nsec it would be wise to select a matched pair for the second and third comparators which control the clock. Propagation effects can be minimized this way.

The decay time clock 20' consists of a set of TTL counters driven by a clock input from quartz crystal oscillator 28 and interfaced to a digital display. An alternative would be a commercial unit such as a Fluke 7261A counter which has a 10 nsec resolution and can be used in such an interval-timer mode. Another alternative is a fast storage oscilloscope at the output of the comparator 16a which has the additional advantage of making the second and third comparators unnecessary; this however is an expensive choice because of the high cost of the storage oscilloscope.

For the most part there is a good deal of freedom in the design of the instrument and requirements on the optical components are rather lax. It is the electronics which bears the brunt of the constraints. Tests were performed using a single frequency argon-ion laser at 514.5 nm. The mode matching lenses were adjusted to obtain reasonable coupling efficiency into the cavity and yet not so much care was taken to avoid coupling to off-axis modes. Two mirrors of a simple back-and-forth cavity were placed 10 meters apart in an evacuated enclosure. Admittedly, this is an unusually large mirror spacing. Tests have been made using smaller open air cavities but the results depended on the ambient air quality. Since a 10 meter interferometer chamber which could be evacuated happened to be available, it was used to render the results independent of the ambient air quality. In practice, a clean air environment may be provided, or a suitable vacuum chamber can be devised for the particular cavity arrangement to be used for testing with this decay time measuring technique.

The overall speed of the electronics was tested by placing the detector in front of the cavity and attenuating the source intensity to simulate light from the cavity. Since light is impinging directly onto the detector, the Pockels cell is immediately switched off upon activation of the comparator circuitry. The decay time was measured to be about 25 nsec. This fall time is dominated by the turn-off time of the Pockels cell; it does not, however inflict a serious limitation to the precision of the decay time measurement for nominal decay time of 0.1 $\mu$s or more. The trigger circuitry is designed to circumvent the problems of incident light intensity fall time. The detector was replaced behind the cavity in order to make a measurement of the cavity decay time.

To verify calibration of the instrument and to demonstrate that the cavity decay is indeed exponential, we first measured the decay time of the cavity. We then chose a resistor and capacitor pair having an RC constant equal to the measured decay time. To well within the 1% uncertainty in the RC component values, the two time constants agreed. The actual decays merged perfectly within the digitalizing accuracy of the oscilloscope. The cavity decay was thus seen to be exponential. Direct measurement of the threshold voltages for clock turn-on and turn-off give a calibration for $e^{-1}$ fall time of 0.5%.

The 10 meter cavity decay time was measured using two different cavities in vacuum: one having low total loss, the other comparatively high loss. Both members of each pair of mirrors came from a single coating run and so were considered identical. In both cases, the cavities consisted of one flat mirror and one curved mirror with a radius of 62 meters.

The decay time for the low loss cavity was 185 $\mu$s$\pm$1.4% where the error is the RMS deviation from the mean of 20 consecutive measurements. Transmission of these mirrors was measured to be 120 ppm. The decay time implies a 180 ppm total loss per mirror: consistent with the transmission measurement and allowing for 60 ppm absorption and scattering loss. The second cavity decayed in 26.24 $\mu$s$\pm$0.2%, indicating a total loss per mirror of 1270 ppm. These mirrors are evidently rather "lossy" as their transmission was measured to be 622 ppm. Note that in both cases the standard error implies a total loss per mirror resolution of 2.5 ppm, (although in the second case the 0.5% timing calibration exceeds the 0.2% spread in decay times). For the record, our measurements give $R=0.999820\pm3$ ppm and $R=0.998730\pm7$ ppm for the low and high loss mirrors, respectively.

Figure 4:
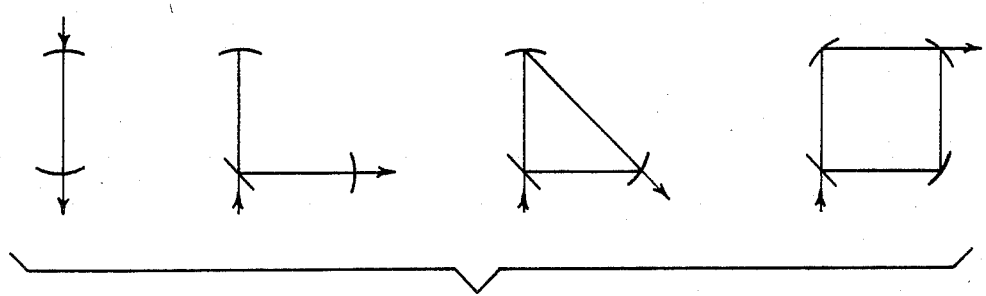
FIG. 4 illustrates various cavity arrangements which may use the present invention.

FIG. 4 illustrates various alternative cavity arrangements of two or more optical elements, both of the round-and-round and of the back-and-forth type, each of which is partially reflecting. To determine the reflectivity of each element, an extra element is substituted for each of the cavity elements to obtain n+1 equations relating n+1 cavity decay time measurements to mirror reflectivity. From that set of equations, the reflectivity of each element is determined. Other parameters may be determined from the formulae given in the table above relating various cavity parameters to the cavity decay time in the low total loss limit discussed hereinbefore. For example, the quality cavity factor, Q, and the total cavity loss, L, may be test parameters for a ring laser gyroscope. Or the same parameters may be quality control parameters for optical coatings used by a manufacturer. The optical elements being coated are simply placed in a test cavity while the cavity decay time, $\tau_c$, is measured. Other examples will occur to one skilled in the art.

The theoretical foundations behind the decay time measurement and under what conditions a measurement of the decay time represents a measure of the mirror characteristics has been discussed. Problems which can be encountered in a measurement have also been discussed. With the decay time and cavity length in hand, one can choose to characterize either the cavity or the mirrors in a variety of ways using the formulae of the table set forth hereinbefore. Or, if one chooses, the measured decay time can be used to infer losses in the mirrors of the cavities. With n mirrors in the cavity, and n+1 mirrors and measurements, it is possible to compute any cavity parameter, as explained hereinbefore with reference to the table of formulae. By readjustment of the position of a mirror, it is possible to test the desired characteristic in different areas of the mirror. By aligning the mirrors of a ring laser gyro, or any optical cavity, for maximum time decay, in situ alignment of the mirrors is accomplished.

The decay time apparatus was designed with a resolution of at least 10 nsec and has exhibited a total loss resolution of at least 5 ppm. This was accomplished by merely measuring the time interval between two voltage levels on the decay curve. One can envision various improvements such as monitoring an entire decay and fitting to it an exponential curve, or improving the clock resolution to better than 10 nsec. We expect the technique could be pushed; nevertheless, this straightforward approach shows very respectable performance using rather simple instrumentation and measurement procedures.

Although particular embodiments of the invention have been described and illustrated herein, it is recognized that modifications and variations may readily occur to those skilled in the art. Consequently, it is intended that the claims be interpreted to cover such modifications and variations.

What is claimed is:

1. A method for making decay time measurements of an optical cavity having at least two reflecting optical elements comprising the steps of
   directing a beam of light into said optical cavity,
   switching the beam of light into said optical cavity off when the beam intensity of the cavity reaches a predetermined threshold level,
   monitoring the beam intensity decay of the optical cavity, and
   measuring the intensity decay time directly.

2. A method as defined in claim 1 used for determining cavity parameters from formulae relating said cavity parameters to the cavity decay time, including the steps of substituting one extra optical element in said cavity for each of the optical elements thereof during separate cavity decay time measurements, and obtaining n+1 cavity decay time measurements for n+1 equations for at least one of said formulae for cavity parameters of interest from which a cavity parameter may be determined for each of the optical elements of said optical cavity.

3. A method as defined in claim 1 wherein said step of measuring cavity decay time is made by digital techniques using a digital counter enabled to count clock pulses from a time when the output beam intensity has decayed exponentially to a level $V_c$ until a time when the output beam intensity has decayed exponentially to a level $(1/e) V_c$, whereby a characteristic decay time $\tau_c$ is obtained.

4. A method as defined in claim 2 wherein said step of measuring cavity decay time is made by digital techniques using a digital counter enabled to count clock pulses from a time when the output beam intensity has decayed exponentially to a level $V_c$ until a time when the output beam intensity has decayed exponentially to a level $(1/e) V_c$, whereby a characteristic decay time $\tau_c$ is obtained.

5. A method as defined in claim 1 wherein said step of measuring cavity decay time is made by analog techniques using a storage oscilloscope the sweep of which is triggered when said beam is switched off to record the actual decay as a function of time from which a characteristic decay time $\tau_c$ is determined.

6. A method as defined in claim 2 wherein said step of measuring cavity decay time is made by analog techniques using a storage oscilloscope the sweep of which is triggered when said beam is switched off to record the actual decay as a function of time from which a characteristic decay time $\tau_c$ is determined.

7. Apparatus for making decay time measurements of an optical cavity having at least two reflecting optical elements comprising means for directing a beam of light into said optical cavity, means for switching off said beam of light into said optical cavity when beam intensity of the cavity reaches a predetermined threshold level, means for monitoring the beam intensity decay of the optical cavity, and means for measuring the intensity decay time directly.

8. Apparatus as defined in claim 7 wherein said means for measuring cavity decay time is comprised of a digital counter, and means for enabling said counter to count clock pulses from a time when the output beam intensity has decayed exponentially to a first level until a time when the output beam intensity has decayed exponentially to a second level, whereby a characteristic decay time $\tau_c$ is obtained for said optical cavity.

9. Apparatus as defined by claim 8 including detector means for monitoring the beam intensity of said optical cavity and producing a signal proportional thereto, and including a source of three reference signals, a first reference signal, a second reference signal below said first reference signal, and a third signal below said second reference signal wherein said means for switching said beam off is comprised of a first means for comparing said detector signal with said first reference signal, and means responsive to said first comparing means for actuating said beam switching means to switch said beam off, second and third comparing means for comparing said detector signal with said second and third reference signals, respectively, and means responsive to said respective second and third comparing means for starting and stopping said digital counter, means for resetting said counter, and means for preventing said switching means from switching said beam on until said digital counter is reset.

10. Apparatus as defined in claim 7 wherein said means for measuring cavity decay time is comprised of a storage oscilloscope, the sweep of which is triggered when said beam is switched off to record the actual decay as a function of time from which a characteristic decay time $\tau_c$ is determined.

11. Apparatus as defined in claim 10 including detector means for monitoring the beam intensity of said optical cavity and producing a signal proportional thereto, and including a source of a reference signal, wherein said means for switching said beam off is comprised of means for comparing said detector signal with said reference signal, means responsive to said comparing means for actuating said beam switching means to switch said beam off and triggering the sweep of said storage oscilloscope on when the detector signal exceeds said reference signal, and means for preventing said beam switching means from being switched on until said preventing means is reset.

* * * * *